United States Patent
Schatzberg et al.

(10) Patent No.: US 6,620,802 B1
(45) Date of Patent: Sep. 16, 2003

(54) METHODS OF TREATING MILD COGNITIVE IMPAIRMENT USING A GLUCOCORTICOID-SPECIFIC RECEPTOR ANTAGONIST

(75) Inventors: Alan F. Schatzberg, Los Altos, CA (US); Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 09/717,703

(22) Filed: Nov. 20, 2000

Related U.S. Application Data
(60) Provisional application No. 60/167,432, filed on Nov. 23, 1999.

(51) Int. Cl.$^7$ .............................................. A61K 31/56
(52) U.S. Cl. ...................................................... 514/178
(58) Field of Search ........................................ 514/178

(56) References Cited

U.S. PATENT DOCUMENTS 6,150,349 A   11/2000   Schatzberg et al.

FOREIGN PATENT DOCUMENTS

| WO | WO 97/37664 | 10/1997 |
| WO | WO 99/59596 A1 | 11/1999 |

OTHER PUBLICATIONS

Aisen, Paul S., "Inflammation and Alzheimer's Disease: Mechanisms and Therapeutic Strategies"; *Gerontology*, 43:143–149 (1997).

Aisen et al., "A Pilot Study of Prednisone in Alzheimer's Disease"; *Dementia*, 7:201–206 (1996).

Aisen et al., "Glucocorticoids in Alzheimer's Disease"; *Drugs & Aging*, 1:1–6 (Jan. 1998).

Aisen, Paul S., "Inflammation and Alzheimer Disease"; *Molecular and Chemical Neuropathology*, 28:83–88 (1996).

Behl et al., "Protection Against Oxidative Stress–induced Neuronal Cell Death—A Novel Role for RU486"; *European Journal of Neuroscience*, 9:912–920 (1997).

Bertagna et al., "The New Steroid Analog RU 486 Inhibits Glucocorticoid Action in Man"; *J Clin Endocrinol Metab*, 59:25–28 (1984).

Cadepond et al., "RU486 (Mifepristone): Mechanisms of Action and Clinical Uses"; *Annu. Rev. Med.*, 48:129–56 (1997).

DeLeon et al., "Cortisol Reduces Hippocampal Glucose Metabolism in Normal Elderly, but Not in Alzheimer's Disease"; *J Clin Endocrinol Metab*, 82:3251–3259 (1997).

Dodt et al., "Different Regulation of Adrenocorticotropin and Cortisol Secretion in Young, Mentally Healthy Elderly and Patients with Senile Dementia of Alzheimer's Type"; *J Clin Endocrinol Metab*, 72:272–276 (1991).

Gerson et al., "Cushing Disease Presenting a Atypical Psychosis Followed by Sudden Death";*Canadian J. Psychiatry*, 30:223 (Apr. 1985).

Greenwald et al., "Cortisol and Alzheimer's Disease, II: Dexamethasone Suppression, Dementia Severity, and Affective Symptoms"; *Am J. Psychiatry*, 143:442–446 (Apr. 1986).

Keenan et al., "The effect on memory of chronic prednisone treatment in patients with systemic disease"; *Neurology*, 47:1396–1402 (Dec. 1996).

Lupien et al., "Basal Cortisol Levels and Cognitive Deficits in Human Aging"; *The Journal of Neuroscience*, 14(5):2893–2903 (May 1994).

Lupien et al., "Cortisol levels during human aging predict hippocampal atrophy and memory deficits"; *Nature Neuroscience*, 1:69 (May 1998).

Lupien et al., "Stress–Induced Declarative Memory Impairment in Healthy Elderly Subjects: Relationship to Cortisol Reactivity"; *J Clin Endocrinol Metab*, 82:2070–2075 (1997).

Maeda et al., "Elevated Urinary Free Cortisol in Patients With Dementia"; *Neurobiology of Aging*, 12:161–163 (1991).

Naimark et al., "Psychotic Symptoms in Parkinson's Disease with Dementia"; *JAGS*, 44:296–299 (1996).

Newcomer et al., "Decreased Memory Performance in Healthy Humans Induced by Stress–Level Cortisol Treatment"; *Arch Gen Psychiatry*, 56:527–533 (Jun. 1999).

Peterson et al., "Mild Cognitive Impairment"; *Arch Neurol.*, 56:303–308 (Mar. 1999).

Peterson et al., "Mild Cognitive Impairment"; *NEUR*, 56:303–308 (1999).

Porter et al., "Stress hormones and brain aging: adding injury to insult?"; *Nature Neuroscience*, 1:3,4 (May 1998).

Saad et al., "Occult Cushing's Disease Presenting with Acute Psychosis"; *The American Journal of Medicine*, 76:759766 (Apr. 1984).

(List continued on next page.)

*Primary Examiner*—Sreeni Padmanabhan
*Assistant Examiner*—San Ming Hui
(74) *Attorney, Agent, or Firm*—Townsend and Townsend and Crew LLP

(57) ABSTRACT

This invention generally pertains to the field of psychiatry. In particular, this invention pertains to the discovery that agents which inhibit the binding of cortisol to its receptors can be used in methods for treating mild cognitive impairment. Mifepristone, a potent specific glucocorticoid receptor antagonist, can be used in these methods. The invention also provides a kit for treating mild cognitive impairment in a human including a glucocorticoid receptor antagonist and instructional material teaching the indications, dosage and schedule of administration of the glucocorticoid receptor antagonist.

13 Claims, No Drawings

OTHER PUBLICATIONS

Sapolsky, Robert M. "The Physiological Relevance of Glucocorticoid Endangerment of the Hippocampus" from *Brain Corticosteroid Receptors: Studies on the Mechanism, Function, and Neurotoxicity of Corticosteroid Action*, Edited by E. Ronald de Kloet, Efrain C. Azmitia, Phillip W. Landfield, ; *Annals of the New York Academy of Sciences*, vol 746 pp. 194–307 (1994).

Talmi et al., "Chronic RU486 Treatment Reduces Age–Related Alterations of Mouse Hippocampal Function"; *Neurobiology of Aging*, 17:9–14 (1996).

Weiner et al., "Cortisol Secretion and Alzheimer's Disease Progression"; *Biol. Psychiatry*, 42:1030–1038 (1997).

Adisalerts on Stn., No. 807126093 Tuor Et al., Protection against hypoxic–ischemic damage with corticosterone and dexomethasone: inhibition of effect by a glucocoricoid antagonist, RU38486, abstract Brain Research vol 743, pp. 258–262 (Dec. 16, 1996.).

METHODS OF TREATING MILD COGNITIVE IMPAIRMENT USING A GLUCOCORTICOID-SPECIFIC RECEPTOR ANTAGONIST

CROSS REFERENCE TO RELATED APPLICATIONS

This application claims the benefit of U.S. Provisional Application No. 60/167,432, filed Nov. 23, 1999, the disclosure of which is incorporated by reference.

FIELD OF THE INVENTION

This invention generally pertains to the field of psychiatry. In particular, this invention pertains to the discovery that agents which inhibit the binding of cortisol to the glucocorticoid receptor can be used in methods of treating mild cognitive impairment (MCI).

INTRODUCTION

MCI is an impairment in cognition, specifically memory performance, that is frequently associated with aging. The degree and type of impairment distinguishes MCI from dementia in that MCI patients exhibit deficits in secondary tests of memory, but perform normally on standard tests measuring other cognitive domains. Thus, MCI is defined as a clinical disorder that is distinct from early stages of dementia, particularly Alzheimer's type dementia, and can therefore be specifically targeted for treatment intervention.

The underlying causes of memory loss in MCI have not been determined, thus a strategy for treatment has not been easily identified. Although some investigators believe that most MCI patients have neuropathology that is characteristic of Alzheimer's disease, many patients diagnosed with MCI typically do not progress to Alzheimer's Disease, thereby suggesting that MCI has an underlying pathophysiology that is divergent from that of Alzheimer's despite other characteristics that may be shared.

A number of treatments for Alzheimer's disease have been proposed, but there is no consensus regarding the etiology of the disease and it is not clear which, if any, of these treatments would also be effective for MCI. Proposed treatments include the use of various agents such as cholinergic agonists (Asthana et al., Clin. Pharmacol. Ther. 60:76–282, 1996), estrogen, Vitamin E (α-tocopherol), nerve growth factors, or calcium blockers to improve memory or slow the rate of neuronal degeneration and death. Alternatively, Alzheimer's disease has been hypothesized to be an inflammatory disease similar to an autoimmune disease and the administration of anti-inflammatory agents has been proposed as a therapy. Ongoing clinical studies based on this hypothesis include those using prednisone, a synthetic cortisol agonist (see, e.g., Aisen, Drugs Aging 12:1–6, 1998; Aisen, Gerontology 43:143–149, 1997; and Aisen, Mol. Chem. Neuropathol. 28:83–88, 1996). In apparent contrast to the latter theory, it has also been observed that patients with dementia can exhibit markedly increased levels of the physiological glucocorticoid cortisol (hydrocortisone) (see, e.g., Davis et al, Am. J. Psych. 143:3, 1986; Maeda et al., Neurobiol Aging 12:161–163, 1991). Moreover, it has been suggested that increased glucocorticoid levels may play a role in pathogenesis.

Cortisol, which is secreted in response to ACTH (corticotropin), shows circadian rhythm variation, and further, is an important element in responsiveness to many physical and psychological stresses. It has been proposed that, with age, the cortisol regulatory system becomes hyperactivated in some individuals, resulting in hypercortisolemia. It has additionally been postulated that high levels of cortisol are neurotoxic, particularly in the hippocampus, a brain structure that is thought to be central to the processing and temporary storage of complex information and memory (see, e.g., Sapolsky et al., Ann. NY Acad. Sci. 746:294–304, 1994; Silva, Annu. Rev. Genet. 31:527–546, 1997; de Leon et al., J. Clin. Endocrinol & Metab. 82:3251, 1997; Maeda et al., supra).

Studies of human subjects who have received treatment with exogenous glucocorticoids at therapeutic levels have suggested that glucocorticoids may play a role in short-term, reversible memory impairment. (see, e.g., Wolkowitz et al., Am J. Psychiatry 147:1297–1303, 1990; Keenan et al., Neurology 47:1396–1402, 1996; Newcomer et al., Arch Gen. Psychiatry 56:527–533, 1999). Furthermore, it has been suggested that basal levels of cortisol that are chronically at the high end of the normal range, i.e., levels that correspond to peak circadian values or approximate those levels seen during stress, contribute to the impaired cognitive performance and loss of hippocampal-mediated memory function observed in aging (see, e.g., Lupien et al., J. Neurosci. 14:2893–2903, 1994; Lupien et al., Nat. Neurosci 1:69–73, 1998).

There has been no evidence prior to this invention, however, that a glucocorticoid receptor antagonist can be an effective treatment for memory impairment in a mature population, especially in patients having cortisol levels that fall within a normal range. Many of the actions of cortisol are mediated by binding to the type I mineral-corticoid receptor, which is preferentially occupied, relative to the type II glucocorticoid receptor, at physiological cortisol levels. As cortisol levels increase, more glucocorticoid receptors are occupied and activated. Thus, those mature individuals who have experienced an aging-associated increase in basal cortisol levels can have a level of glucocorticoid activity that, with time, directly or indirectly results in impaired memory function. Inhibition of glucocorticoid receptor activity is therefore desirable in those individuals. Because cortisol plays an essential role in metabolism, inhibition of all cortisol-mediated activities, however, would be fatal. Therefore, antagonists that specifically prevent type II glucocorticoid receptor functions, but do not antagonize type I mineralcorticoid receptor functions are of particular use in this invention. RU486 and similar antagonists are examples of this category of receptor antagonists.

RU486 has been noted as being effective at abrogating some of the age-associated electrophysiological changes in the rat hippocampus (Talmi et al., Neurobiol. of Aging 17:9–14, 1996) and also as providing protection against oxidative stress-induced neuronal cell death in the mouse hippocampus (Behl et al., European J. of Neuorsci. 9:912–920, 1997). There have been no studies, however, that have shown that RU486 can improve memory function.

The present inventors have determined that glucocorticoid receptor antagonists such as RU486 are effective agents for the specific treatment of age-associated memory impairment that is not affiliated with dementia in mature patients with normal cortisol levels. The present invention therefore fulfills the need for an effective treatment for MCI by providing methods of administering glucocorticoid receptor antagonists to improve memory function in patients diagnosed with MCI.

SUMMARY OF THE INVENTION

The invention provides a method of treating a patient diagnosed with mild cognitive impairment (MCI) who is 45 years or older and has normal cortisol levels. The method comprises administration of a therapeutically effective amount of a glucocorticoid receptor antagonist to the patient, wherein the patient: (i) obtains at least one perfect score on the folstein Mini Mental status Exam in three administrations of the Exam; (ii) has a clinical dementia rating (CDR) of 0.5; and (iii) scores below, preferably by 1.5 or more standard devations, the age- and education-adjusted cutoff on a memory task test, typically, the logical memory II subscale (Delayed Paragraph Recall) of a paragraph test. The amount of glucocorticoid receptor antagonist administered will preferably improve performance on such a memory task test.

In one embodiment of the invention, the method of treating MCI uses a glucocorticoid receptor antagonist comprising a steroidal skeleton with at least one phenyl-containing moiety in the 11-beta position of the steroidal skeleton. The phenyl-containing moiety in the 11-beta position of the steroidal skeleton can be a dimethylaminophenyl moiety. In alternative embodiments, the glucocorticoid receptor antagonist comprises mifepristone, or, the glucocorticoid receptor antagonist is selected from the group consisting of RU009 and RU044.

In other embodiments, the glucocorticoid receptor antagonist is administered in a daily amount of between about 0.5 to about 20 mg per kilogram of body weight per day; between about 1 to about 10 mg per kilogram of body weight per day; or between about 1 to about 4 mg per kilogram of body weight per day. The administration can be once per day. In alternative embodiments, the mode of glucocorticoid receptor antagonist administration is oral, or by a transdermal application, by a nebulized suspension, or by an aerosol spray.

The invention also provides a kit for the treatment of MCI in a human, the kit comprising a glucocorticoid receptor antagonist; and, an instructional material teaching the indications, dosage and schedule of administration of the glucocorticoid receptor antagonist. In alternative embodiments, the instructional material indicates that the glucocorticoid receptor antagonist can be administered in a daily amount of about 0.5 to about 20 mg per kilogram of body weight per day, of about 1 to about 10 mg per kilogram of body weight per day, or about 1 to about 4 mg per kilogram of body weight per day. The instructional material can indicate that corticol contributes to the memory impairment in patients with MCI, and that the glucocorticoid receptor antagonist can be used to treat MCI. In one embodiment, the glucocorticoid receptor antagonist in the kit is mifepristone. The mifepristone can in tablet form.

A further understanding of the nature and advantages of the present invention is realized by reference to the remaining portions of the specification and claims.

All publications, patents and patent applications cited herein are hereby expressly incorporated by reference for all purposes.

DEFINITIONS

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being; or, in some situations, preventing the onset of dementia. The treatment or amelioration of symptoms can be based on objective or subjective parameters; including the results of a physical examination, neuropsychiatric exams, and/or a psychiatric evaluation. For example, the methods of the invention successfully treat a patient's MCI by improving performance of memory task tests and/or slowing or preventing the rate of, or extent of, cognitive decline.

The term "mild cognitive impairment (MCI)" refers to a category of memory and cognitive impairment that is typically characterized by a clinical dementia rating (CDR) of 0.5 (see, e.g., Hughes et al., *Brit. J. Psychiat.* 140:566–572, 1982) and further characterized by memory impairment, but not impaired function in other cognitive domains. Memory impairment is preferably measured using tests such as a "paragraph test". A patient diagnosed with MCI often exhibits impaired delayed recall performance. MCI is typically associated with aging and generally occurs in patients who are 45 years of age or older.

The term "dementia" refers to a psychiatric condition in its broadest sense, as defined in American Psychiatric Association: Diagnostic and Statistical Manual of Mental Disorders, Fourth Edition, Washington, D.C., 1994 ("DSM-IV"). The DSM-IV defines "dementia" as characterized by multiple cognitive deficits that include impairments in memory and lists various dementias according to presumed etiology. The DSM-IV sets forth a generally accepted standard for such diagnosing, categorizing and treating of dementia and associated psychiatric disorders.

The term "cortisol" refers to a family of compositions also referred to hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha(1-propynyl)-estra-4,9-dien-3-one), or 11-beta-(4-dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/ mediated by the binding of any cortisol or cortisol analogue to a GR receptor. Chemical names for RU-486 vary; for example, RU486 has also been termed: 11B-[p-(Dimethylamino)phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B, 17B)-11-[4-dimethylamino)phenyl]-17-hydroxy-17-(1-propynyl)estra-4,9-dien-3-one; and 11B-[4-(N,N-dimethylamino)phenyl]-17A-(prop-1-ynyl)-D-4,9-estradiene-17B-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralcorticoid receptor (MR) at a rate of at least 100-fold, and frequently 1000-fold.

DETAILED DESCRIPTION OF THE INVENTION

This invention pertains to the surprising discovery that agents that can inhibit a biological response caused by an agonist-occupied glucocorticoid receptor GR are effective for treating MCI. In treating MCI, the methods of the invention can preferably improve the impairment of memory, and/or, the rate of, or extent of, any further decline in memory function In one embodiment, the methods of the invention use agents that act as GR antagonists, blocking the interaction of cortisol with GR, to treat or ameliorate MCI. The methods of the invention are effective in improving memory performance, or preventing or slowing further memory impairment, in an MCI patient afflicted with either normal or increased levels of cortisol or other glucocorticoids, natural or synthetic.

Cortisol acts by binding to an intracellular, glucocorticoid receptor (GR). In man, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

The biologic effects of cortisol; including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation<10-9 M (Cadepond, *Annu. Rev. Med.* 48:129, 1997). Thus, in one embodiment of the invention, mifepristone and related compounds are used to treat MCI.

MCI can be manifested as mental or psychological deficits that include impairment in memory, but normal function in other cognitive domains. Thus, a variety of means of diagnosing MCI and assessing the success of treatment, i.e., the success and extent the MCI is treated by the methods of the invention, can be used, and a few exemplary means are set forth herein. These means can include classical, subjective psychological evaluations and neuropsychiatric examinations as described below.

As the methods of the invention include use of any means to inhibit the biological effects of an agonist-bound GR, illustrative compounds and compositions which can be used to treat MCI are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

4. Diagnosis of MCI

MCI is characterized as a mild impairment of cognition categorized as a CDR of 0.5 that is associated with deficits in a memory task test, such as a paragraph test. An MCI patient is fully oriented, but demonstrates mild consistent forgetfulness. Impairment in cognitive domains other than memory, such as problem solving and judgment is doubtful, if present at all, and, further, the MCI patient does not demonstrate impairment in functioning in the community or at home. A patient with MCI scores normally on standard tests of dementia.

There are various means to diagnose the onset of MCI and to assess the efficacy of treatment using the methods of the invention. These include the administration of psychiatric tests to determine the CDR, the administration of memory tests, and the administration of psychiatric tests for dementia, which are used to exclude a diagnosis of dementia. The results of these test may be considered in conjuction with other objective physical tests as described below. These means are also useful for assessing the efficacy of the methods of the invention in improving memory or decreasing or diminishing further impairment in memory or cognitive decline in a patient with MCI. While the practitioner can use any set of prescribed or empirical criteria that are defined in the scientific and patent literature to diagnose the presence of MCI as an indication to practice the methods of the invention, some illustrative diagnostic guidelines and examples of relevant symptoms and conditions are described below. Subjective and objective criteria can be used to measure and assess the success of a particular GR antagonist, pharmaceutical formulation, dosage, treatment schedule or regimen. The features (symptoms) of and criteria for diagnosing MCI are described, e.g., in Petersen et al., *Arch. Neurol.* 56:303–308, 1999.

a. Assessing and Diagnosing MCI

MCI can be diagnosed by formal psychiatric assessment using subjective diagnosis or objective test criteria to determine whether an individual is afflicted with MCI. The methods of the invention are preferably practiced early in the course of (in the early stages of) MCI, and most preferably, at the first sign of the disease. This is especially critical in the case of MCI patients who may be at risk for progression to Alzheimer's Disease, for example, patients who bear the apolipoprotein E $\epsilon$4 genotype (see, e.g., Tierney et al., *Neurology* 45:149–154, 1996).

MCI can be diagnosed and evaluated using any of the many objective tests or criteria well-known and accepted in the fields of psychology or psychiatry. Objective tests can used to determine whether an individual is suffering from impaired memory function or dementia and to measure and assess the success of a particular GR antagonist, pharmaceutical formulation, dosage, treatment schedule or regimen. For example, measuring changes in cognitive ability and memory aids in the diagnosis and treatment assessment of a patient MCI. Any test known in the art can be used.

One criterion for the diagnosis of MCI is that the patient receives a CDR of 0.5 as described, e.g., in Hughes et al., *Brit. J. Psychiat.* 140:566–572, 1982 and Morris, *Neurology* 43:2412–2414, 1993. In determining the CDR, a patient is typically assessed and rated in each of six cognitive and behavioural categories: memory, orientation, judgement and problem solving, community affairs, home and hobbies, and personal care. The assessment may include historical information provided by the patient, or preferably, a corroborator who knows the patient well. The patient is assessed and rated in each of these areas and the overall rating, (0, 0.5, 1.0, 2.0 or 3.0) determined. A rating of 0 is considered normal. A rating of 1.0 is considered to correspond to mild dementia. A patient with a CDR of 0.5 is characterized by mild consistent forgetfulness, partial recollection of events and "benign" forgetfulness. The patient is fully oriented and exhibits little impairment in determining similarities and differences and other problem solving skills, or impairment in function in terms of the community, home, or personal care.

A hallmark of MCI is impaired performance on a memory task test. Memory may be measured by such tests known in the art as the Wechsler Memory Scale or a pair-associated memory task. A patient is considered to exhibit impaired performance on such a test if the score is below the education and age-adjusted cutoff for that test. MCI is typically characterized by impairment in delayed recall memory functions, which can be specifically addressed as a component of a memory task test. For example, impaired memory function may be documented by scoring at or below the education cutoff on the Logical Memory II subscale (Delayed Paragraph Recall) from the Wechsler Memory Scale-Revised, of which the maximum score is 25. Age and education-adjusted cutoffs are determined using methods known in the art (see, e.g., Ivnik et al. *Clinc. Neuropsychol* 6 (Suppl):1–30 and 49–82, 1992; Ivnik et al. *J. Consult Clin. Psychol* 3: 1991; Ivnik et al., *Clin. Neuropsychol.* 10:262–276, 1996) An example of these cutoffs are: a) less than or equal to 8 for 16 or more years of education; b) less than or equal to 4 for 8–15 years of education and c) less than or equal to 2 for 0–7 year of education. A cutoff value may be determined, for example, by selecting a value that is 1, preferably 1.5, or more standard deviations from the norm for that education and age cohort.

"Improvement" in memory is present within the context of the present invention if there is a statistically significant difference in the direction of normality between the performance of patients treated using the methods of the invention as compared to members of a placebo group or between subsequent tests given to the same patient.

In order to diagnose MCI, a patient must also be categorized as not being demented. Accordingly, a diagnosis of MCI includes neuropychological evaluation for dementia. The criteria for dementia are described, e.g., in the DSM-IV, supra. While the practitioner can use any criteria or means to evaluate dementia, the DSM-IV sets forth a generally accepted standard for such diagnosing, categorizing and treating dementia and associated psychiatric disorders, including Alzheimer's disease and multi-infarct dementia. Several illustrative examples of such criteria utilized in the methods of the invention are set forth below.

One objective test for dementia is the so-called Mini-Mental State Examination (MMSE), as described by Folstein "'Mini-mental state.' A practical method for grading the cognitive state of patients for the clinician." *J. Psychiatr. Res.* 12:189–198, 1975. The MMSE evaluates the the presence of global intellectual deterioration. See also Folstein "Differential diagnosis of dementia. The clinical process." *Psychiatr Clin North Am.* 20:45–57, 1997. The MMSE is a long-recognized means to evaluate the onset of dementia and the presence of global intellectual deterioration, as seen in Alzheimer's disease and multi-infart dementia. See, e.g., Kaufer, *J. Neuropsychiatry Clin. Neurosci.* 10:55–63, 1998; Becke, *Alzheimer Dis Assoc Disord.* 12:54–57, 1998; Ellis, *Arch. Neurol.* 55:360–365, 1998; Magni, *Int. Psychogeriatr.* 8:127–134, 1996; Monsch, *Acta Neurol. Scand.* 92:145–150, 1995. The MMSE is scored from 1 to 30. The MMSE does not evaluate basic cognitive potential, as, for example, the so-called IQ test. Instead, it tests intellectual skills. A person of "normal" intellectual capabilities will score a "30" on the MMSE objective test (however, a person with a MMSE score of 30 could also score well below "normal" on an IQ test). Accordingly, the methods of the invention are appropriately administered when an individual scores 30 on the MMSE. Because it is possible for a "normal" individual to score less than 30 upon a single administration of a test, a "normal" indication on the test is considered to be a score of 30 on at least one test in three administrations of the test.

Another means to evaluate dementia, particularly Alzheimer's disease, is the Alzheimer's Disease Assessment Scale (ADAS-Cog), or a variation termed the Standardized Alzheimer's Disease Assessment Scale (SADAS). It is commonly used as an efficacy measure in clinical drug trials of Alzheimer's disease and related disorders characterized by cognitive decline. SADAS and ADAS-Cog were not designed to diagnose Alzheimer's disease; they are useful in characterizing symptoms of dementia and are a relatively sensitive indicator of dementia progression. (See, e.g., Doraiswamy, *Neurology* 48:1511–1517, 1997; and Standish, *J. Am. Geriatr. Soc.* 44:712–716, 1996.) The evaluation for the presence of MCI can also utilize a combination of subjective diagnosis and objective testing. For example, family history and history provided by the patient as well as other individuals can be used as a component in the determination of MCI. Other tests may also be considered in diagnosing MCI. In one study (Petersen et al., *Arch Nuerol.* 56:303–308, 1999), patients were seen by a behavioral neurologist who obtained a medical history from the patients and corroborating sources, and performed a variety of tests including the Short Test of Mental Status, Hachinski Ischemic Scale, and a neurologic examination. Other data collected included the Record of Independent Living, Geriatric Depression Scale, and additional family history information. as well as laboratory tests such as a chemistry group, complete blood cell count, vitamin $B_{12}$ and folic acid levels, and thryroid-stimulating hormone levels. In this study, the first set of tests used for diagnostic purposes included the Wechsler Adult Intelligence Scale-Revised, Wechsler Memory Scale-Revised, Auditory verbal learning Test and Wide-Ragne Achievement test-III. A second set of tests, which were used for research purposes, included the Mini-Mental State Examination, dememntia rating Scale, Free and Cued Selective Reminding test, Boston Naming Test, controlled Oral Word Assocation Test and category fluency procedures.

2. General Laboratory Procedures

A number of general laboratory tests can be used to assist in the diagnosis, progress and prognosis of the patient with MCI, including monitoring of parameters such as blood cortisol, drug metabolism, brain structure and function and the like can be practiced with the methods of the invention. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol, especially high levels of cortisol, have been associated with dementia and the rate and degree of cognitive decline. For example, among individuals with early-stage Alzheimer's disease who do not have apolipoprotein E4 alleles, a higher baseline cortisol measure is associated with a significantly greater rate of decline in cognitive function. Thus, monitoring blood cortisol and determining baseline cortisol levels is a useful laboratory test to aid in the diagnosis, treatment and prognosis of an MCI patient. A wide variety of laboratory tests exist that can be used to determine whether an individual is normal, hypo- or hypercortisolemic. MCI patients typically have normal levels of cortisol that are often less than 25 $\mu$g/dl in the afternoon, and frequently about 15 μg/dl or less in the afternoon, although the values often fall at the high end of the normal range, which is generally considered to be 5–15 μg/dl in the afternoon.

Immunoassays such as radioimmunoassays are commonly used because they are accurate, easy to do and relatively cheap. Because levels of circulating cortisol is an indicator of adrenocorticol function, a variety of stimulation and suppression tests, such as ACTH Stimulation, ACTH Reserve, dexamethasone suppression test (see, e.g., Greenwald, *Am. J. Psychiatry* 143:442–446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), *Acta Psychiatr. Scand.* 70:239–247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor pre-dilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat dementia, an illustrative example of determining blood and urine mifepristone levels is set forth in the Example below.

c. Other Laboratory Procedures

Because MCI can be heterogeneous, a number of additional laboratory tests can be used adjunctively in the methods of the invention to assist in diagnosis, treatment efficacy, prognosis, toxicity and the like. For example, as increased hypercortisolemia has also been associated with cognitive decline, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, and/or total and free testosterone.

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401–406, 1987.

3. Glucocorticoid Receptor Antagonists to Treat MCI

The invention provides for methods of treating MCI utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists

Steroidal glucocorticoid antagonists are administered for the treatment of MCI in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557–563, 1989).

i.) Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. Ibid). Preferred embodiments of the invention include all 11-beta-aryl steroid backbone derivatives because these compounds are devoid of progesterone receptor (PR) binding activity (Agarwal *FEBS* 217:221–226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)-17-alpha-(1-propynyl) estra-4,9-dien-3-one). Mifepristone has been shown to be a powerful antagonist of both the progesterone and glucocorticoid (GR) receptors. Another 11-beta phenylaminodimethyl steroids shown to have GR antagonist effects includes RU009 (RU39.009), 11-beta-(4-dimethyl-aminoethoxyphenyl)-17-alpha-(propynyl-17-beta-hydroxy-4,9-estradien-3-one) (see Bocquel, *J. Steroid Biochem. Molec. Biol.* 45:205–215, 1993). Another GR antagonist related to RU486 is RU044 (RU43.044) 17-beta-hydrox-17-alpha-19-(4-methyl-phenyl)-androsta-4,9 (11)-dien-3-one) (Bocquel, 1993, supra). See also Teutsch, *Steroids* 38:651–665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons, *J. Steroid Biochem.* 24:25–32 1986; Mercier, *J. Steroid Biochem.* 25:11–20, 1986; U.S. Pat. No. 4,296,206.

ii). Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, *Nature* 279:158–160, 1979).

iii). Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, *Endocrinology* 107:1278–1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoidal activity in comparison to 17-propinyl side chain containing compounds.

b. Non-Steroidal Anti-Glucocorticoids as Antagonists

Non-steroidal glucocorticoid antagonists are also used in the methods of the invention to treat MCI. These include synthetic mimetics and analogs of proteins, including partially peptidic, pseudopeptidic and non-peptidic molecular entities. For example, oligomeric peptidomimetics useful in the invention include (alpha-betaunsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297–304, 1994; de Bont, *Bioorganic & Medicinal Chem.* 4:667–672, 1996). The creation and simultaneous screening of large libraries of synthetic molecules can be carried out using well-known techniques in combinatorial chemistry, for example, see van Breemen, *Anal Chem* 69:2159–2164, 1997; and Larn, *Anticancer Drug Des* 12:145–167, 1997. Design of peptidomimetics specific for GR can be designed using computer programs in conjunction with combinatorial chemistry (combinatorial library) screening approaches (Murray, *J. of Computer-Aided Molec. Design* 9:381–395, 1995; Bohm, *J. of Computer-Aided Molec. Design* 10:265–272, 1996). Such "rational drug design" can help develop peptide isomerics and conformers including cycloisomers, retro-inverso isomers, retro isomers and the like (as discussed in Chorev, *TibTech* 13:438–445, 1995).

c. Identifying Specific Glucocorticoid Receptor Antagonists

Because any specific GR antagonist can be used for the treatment of MCI in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, *Meth. Enzymol.* 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162–168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313–318, 1992). As another example, the ability of a putative GR antagonist to block nuclear binding of $^3$H-dexamethasone-GR complex can be used (Alexandrova et al., *J. Steroid Biochem. Mol. Biol.* 41:723–725, 1992). To further identify putative GR antagonists, kinetic assays able to discriminate between glucocorticoid agonists and antagonists by means of receptor-binding kinetics can also be used (as described in Jones, *Biochem J.* 204:721–729, 1982).

In another illustrative example, the assay described by Daune, *Molec. Pharm.* 13:948–955, 1977; and in U.S. Pat. No. 4,386,085, can be used to identify anti-glucocorticoid activity. Briefly, the thymocytes of surrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. No. : 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticod receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J. Steroid Biochem Molec. Biol.* 45:205–215, 1993, U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

4. Treatment of MCI using Glucocorticoid Receptor Antagonists

Antiglucocorticoids, such as mifepristone, are formulated as pharmaceuticals to be used in the methods of the invention to treat MCI. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of dementia, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in appropriate and suitable dosages. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers. In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93–102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example, sweetening, flavoring and coloring agents, can also be present.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187–1193, 1995; Tjwa, *Ann. Allergy Asthma Immunol.* 75:107–111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623–645, 1995; as biodegradable and injectable gel formulations (see, e.g., Gao *Pharm. Res.* 12:857–863, 1995); or, as microspheres for oral administration (see, e.g., Eyles, *J. Pharm. Pharmacol.* 49:669–674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, that is combined with buffer prior to use In another embodiment, the GR antagonist formulations of the invention are useful for parenteral administration, such as intravenous (IV) administration or administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293–306, 1996; Chonn, *Curr. Opin. Biotechnol.* 6:698–708, 1995; Ostro, *Am. J. Hosp. Pharm.* 46:1576–1587, 1989).

b. Determining Dosing Regimens for Glucocorticoid Receptor Antagonists

The methods of the invention treat MCI, i.e., improve memory function, prevent or diminish the rate of further memory impairment. The amount of GR antagonist adequate to accomplish this is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J. Steroid Biochem. Mol. Biol.* 58:611–617; Groning (1996)

*Pharmazie* 51:337–341; Fotherby (1996) *Contraception* 54:59–69; Johnson (1995) *J. Pharm. Sci.* 84:1144–1146; Rohatagi (1995) *Pharmazie* 50:610–613; Brophy (1983) *Eur. J. Clin. Pharmacol.* 24:103–108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the dementia. Thus, one typical pharmaceutical formulations for oral administration of mifepristone is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for the treatment of dementia in a human which includes a GR antagonist and instructional material teaching the indications, dosage and schedule of administration of the GR antagonist.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Treating MCI with Mifepristone

The following example demonstrates how to practice the methods of the invention.

Patient Selection

Individuals are diagnosed with MCI using subjective and objective criteria, including criteria as set forth by the National Institute of Neurological Diseases and Stroke (NINCDS) and the DSM-IV, as described above. A patient is diagnosed as having MCI if the patient receives a CDR of 0.5, shows deficits in performance of a memory task test, typically a paragraph recall test, and who tests "normal", i.e., 30, on a Folstein Mini Mental Status exam. The MCI patient is typically 45 years or older and has normal levels of cortisol for his or her age.

Dosage Regimen and Administration of Mifepristone

The glucocorticoid receptor (GR) antagonist, mifepristone, is used in this study. It is administered in dosages of 200 mg daily. Individuals will be given 200 mg of mifepristone daily for six months and evaluated as described below. Dosages will be adjusted if necessary and further evaluations will be performed periodically throughout treatment.

Mifepristone tablets are available from Shanghai HuaLian Pharmaceuticals Co., Ltd., Shanghai, China.

Assessing Treatment of MCI

To delineate and assess the effectiveness of mifepristone in improving memory impairment or preventing or slowing further memory impairment, formal psychiatric assessment and a battery of neuro-psychological tests and assessments are administered to all patients. The patients' CDR will be determined and performance on memory task tests such as the paragraph recall test will be assessed. Patients will additionally undergo MMSE assessment to determine status with respect to dementia.

These tests and diagnostic assessments take place at baseline (patient's entry into treatment) and periodically throughout treatment. The battery of tests include measures of verbal and nonverbal memory; and test for dementia including executive functions, such as abstract reasoning and problem solving; language, including both confrontation naming and word fluency; visuospatial and visuoperceptual abilities; and attention.

Example 2

Measuring Cortisol Levels

To measure cortisol levels of the patients of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15–28° C.) by gentle swirling or inversion. Sixteen tubes in duplicate at 25 microliters of serum per tube are prepared. Cortisol concentrations is calculated from the prepared calibration tubes. Net counts equals the average CPM minus the average non-specific CPM. Cortisol concentrations for the unknowns is estimated by interpolation from the calibration curve (Dudley, et al. (1985) Clin. Chem. 31:1264–1271).

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of treating mild cognitive impairment comprising administering a therapeutically effective amount of an antagonist specific for the Type II glucocorticoid receptor to a patient diagnosed with mild cognitive impairment who is 45 years or older and has normal levels of cortisol for a human population of their age said amount of antagonist effective to treat cognitive impairment, wherein the patient meets the following criteria:

(i) obtains at least one perfect score on the Folstein Mini Mental Status Exam in three administrations of said Exam;
   (ii) receives a rating of 0.5 on the Clinical Dementia Rating Scale, and
   (iii) scores 1.5 standard deviations or below the age- and education-adjusted normal value on a paragraph recall test.

2. The method of claim 1, wherein the amount of glucocorticoid receptor antagonist will prophylactically treat further memory impairment.

3. The method of claim 1, wherein the amount of glucocorticoid receptor antagonist will improve performance on a paragraph recall test.

4. The method of claim 1, wherein the glucocorticoid receptor antagonist comprises a steroidal skeleton with at least one phenyl-containing moiety in the 11-beta position of the steroidal skeleton.

5. The method of claim 4, wherein the phenyl-containing moiety in the 11-beta position of the steroidal skeleton is a dimethylaminophenyl moiety.

6. The method of claim 4, wherein the glucocorticoid receptor antagonist comprises mifepristone.

7. The method of claim 4, wherein the glucocorticoid receptor antagonist is selected from the group consisting of 11-beta-(4-dimethylaminoethoxyphenol)-17-alpha-(propynyl-17-beta-hydroxy-4,9-estradien-3-one) and 17-beta-hydrox-17-alpha-19-(4-methyl-phenyl)-adrosta-4,9(11)-dien-3-one).

8. The method of claim 1, wherein the glucocorticoid receptor antagonist is administered in a daily amount of between about 0.5 to about 20 mg per kilogram of body weight per day.

9. The method of claim 8, wherein the glucocorticoid receptor antagonist is administered in a daily amount of between about 1 to about 10 mg per kilogram of body weight per day.

10. The method of claim 9, wherein the glucocorticoid receptor antagonist is administered in a daily amount of between about 1 to about 4 mg per kilogram of body weight per day.

11. The method of claim 1, wherein the administration is once per day.

12. The method of claim 1, wherein the mode of administration is oral.

13. The method of claim 1, wherein the mode of administration is by a transdermal application, by a nebulized suspension, or by an aerosol spray.

* * * * *